(12) United States Patent
Kusaki et al.

(10) Patent No.: US 8,343,548 B2
(45) Date of Patent: *Jan. 1, 2013

(54) SOLID DOSAGE FORM COMPRISING SOLID DISPERSION

(75) Inventors: Fumie Kusaki, Joetsu (JP); Takafumi Hoshino, Joetsu (JP); Naosuke Maruyama, Joetsu (JP); Yuichi Nishiyama, Joetsu (JP); Ikuo Fukui, Joetsu (JP); Hiroshi Umezawa, Joetsu (JP)

(73) Assignee: Shin-Etsu Chemical Co., Ltd. (JP)

( * ) Notice: Subject to any disclaimer, the term of this patent is extended or adjusted under 35 U.S.C. 154(b) by 811 days.

This patent is subject to a terminal disclaimer.

(21) Appl. No.: 11/888,529

(22) Filed: Aug. 1, 2007

(65) Prior Publication Data

US 2008/0038340 A1 Feb. 14, 2008

(30) Foreign Application Priority Data

Aug. 8, 2006 (JP) .................................. 2006-215401
Oct. 23, 2006 (JP) .................................. 2006-287860

(51) Int. Cl.
*A61K 9/14* (2006.01)
*A61K 9/50* (2006.01)

(52) U.S. Cl. ........................................ 424/489; 424/499

(58) Field of Classification Search ........................ None
See application file for complete search history.

(56) References Cited

U.S. PATENT DOCUMENTS

| | | | |
|---|---|---|---|
| 3,852,421 A | 12/1974 | Koyanagi et al. | |
| 4,091,205 A | 5/1978 | Onda et al. | |
| 5,028,433 A | 7/1991 | Ishimaru et al. | |
| 5,340,591 A | 8/1994 | Nakano et al. | |
| 6,525,192 B2 | 2/2003 | Obara et al. | |
| 6,884,883 B1 | 4/2005 | Shima et al. | |
| 7,939,101 B2 * | 5/2011 | Obae et al. | 424/465 |
| 2002/0016452 A1 | 2/2002 | Obara et al. | |
| 2003/0125543 A1 | 7/2003 | Obara et al. | |
| 2003/0224043 A1 | 12/2003 | Appel et al. | |
| 2004/0167224 A1 | 8/2004 | Ozaki et al. | |
| 2006/0204572 A1 * | 9/2006 | Higuchi et al. | 424/464 |

FOREIGN PATENT DOCUMENTS

| | | |
|---|---|---|
| EP | 0497331 A2 | 8/1992 |
| EP | 0662320 A1 | 7/1995 |
| EP | 1054019 A1 * | 11/2000 |
| EP | 1099709 A1 | 5/2001 |
| EP | 1319670 A1 | 6/2003 |
| EP | 1514547 A1 | 3/2005 |
| EP | 1854463 A1 | 11/2007 |
| EP | 1967211 A1 | 9/2008 |
| GB | 1479557 | 7/1977 |
| JP | 73-038858 B | 11/1973 |
| JP | 1982-053100 B | 11/1982 |
| JP | 5-262642 A | 10/1993 |
| JP | 7-324101 A | 12/1995 |
| JP | 9-076233 A | 3/1997 |
| JP | 10-305084 A | 11/1998 |
| JP | 11-322802 A | 11/1999 |
| JP | 2001-009316 A | 1/2001 |
| JP | 2004-067606 A | 3/2004 |
| JP | 2005-517690 A | 6/2005 |
| JP | 2005-517690 W | 6/2005 |
| WO | WO 97/46224 A1 | 12/1997 |
| WO | WO 00/57881 A1 | 10/2000 |
| WO | WO 03/063831 A2 | 8/2003 |
| WO | WO 2004/058257 A1 | 7/2004 |
| WO | WO 2005/046696 A1 | 5/2005 |
| WO | WO 2007/108010 A2 | 9/2007 |

OTHER PUBLICATIONS

Alvarez-Lorenzo et al. "Evaluation of low-substituted hydroxypropylcelluloses (L-HPCs) as filler-binders for direct compression" *International J. of Pharmaceutics* 197:107-116 (2000).
European search report corresponding to European Patent Application No. 07015394.5-1214 dated Mar. 5, 2008.
Chinese Office Action corresponding to Chinese Patent Application No. 200710140179.0 mailed Jul. 23, 2009.
Hirasawa et al. "Stability of Nilvadipine Solid Dispersion Tablet with Non-Packaging Condition", *J. Pharm. Soc. of Japan Yakugaku Zasshi* 124(1) 19-23 (2004) Partial translation pf p. 19, line 16 to p. 20, line 27.
R. J. Harwood "Hydroxypropyl Cellulose, Low-substituted", Handbook of Pharmaceutical Excipients, 5th Ed., *Pharmaceutical Press* pp. 341-343 (2006).
European Search Report corresponding to European Patent Application No. 07015395.2 mailed Oct. 2, 2009.
European Search Report corresponding to European Patent Application No. 07015396.0 mailed Oct. 2, 2009.
Japanese Office Action corresponding to Japanese Application No. 2007-206387 mailed Jun. 1, 2012.
Japanese Office Action corresponding to Japanese Application No. 2007-206388 mailed Apr. 13, 2012.
Japanese Office Action corresponding to Japanese Application No. 2007-206389 mailed Mar. 27, 2012.

* cited by examiner

*Primary Examiner* — Susan Tran
(74) *Attorney, Agent, or Firm* — Myers Bigel Sibley & Sajovec, PA

(57) ABSTRACT

Provided are a solid dosage form comprising an enteric solid dispersion that allows a drug in the preparation to be rapidly dissolved without compromising the solubility of the solid dispersion, and a method for producing the same. More specifically, provided is a solid dosage form comprising an enteric solid dispersion comprising a poorly soluble drug, an enteric polymer and a disintegrant, wherein the disintegrant is low-substituted hydroxypropylcellulose having an average particle size of 10 to 100 μm and a specific surface area measured by BET method of at least 1.0 m$^2$/g. Moreover, provided is a method for producing a solid dosage form comprising an enteric solid dispersion, the method comprising steps of: spraying an enteric polymer solution in which a poorly soluble drug has been dispersed or dissolved, on a powder of low-substituted hydroxypropylcellulose having an average particle size of 10 to 100 μm and a specific surface area measured by BET method of at least 1.0 m$^2$/g and serving as a disintegrant; and granulating the resultant; and drying.

12 Claims, No Drawings

SOLID DOSAGE FORM COMPRISING SOLID DISPERSION

CROSS-REFERENCE TO RELATED APPLICATION

The present application claims priority to Japanese Patent Application Nos. 2006-215401, filed Aug. 8, 2006 and 2006-287860, filed Oct. 23, 2006, the disclosures of which are incorporated herein by reference in their entirety.

BACKGROUND OF THE INVENTION

1. Field of the Invention

The present invention relates to a solid dosage form of an enteric solid dispersion produced for improving the solubility of a poorly soluble drug and a method for producing the same. In particular, the present invention relates to a solid dosage forms of an enteric solid, comprising the solid dispersion, that rapidly can be disintegrated and allow a drug to be dissolved, and a method for producing the same.

2. Description of the Related Art

Poorly soluble drugs have high crystallinity and extremely low solubility in water. Thus, bioavailability or internal absorption of preparations produced from these drugs is low, and thus there is the problem that the drug action is insufficient. As a technique for solving this problem, a solid dispersion has been developed in which molecules of a poorly soluble drug are dispersed in a high molecular weight carrier, such as a cellulose derivative, in an amorphous state.

Conventional solid dispersions are used as preparations in the form of capsules containing a solid obtained by spray-drying a cosolvent in which a poorly soluble drug and a carrier are dissolved, or in the form of fine granules or granules as they are. However, the form of tablets, which is a commonly solid dosage form, is most preferable because tablets are easily prescribed and used in a fixed dose, and easily handled and used by patients in use.

It is known that in the case of tablets produced from a solid dispersion powder, the porosity of the tablets is often lowered not only due to a reduced specific surface area, but also due to plastic deformation of amorphous drug molecules during a compression process and strong compressibility between high molecular weight carrier particles. This low porosity leads to slow permeation of water molecules into the tablets in administration, and to slow disintegration of the tablets, and thus the solid dispersion cannot exert its original effect of improving the solubility. Furthermore, the viscosity of a water-soluble high molecular weight substance or enteric high molecular weight substance serving as a carrier increases during hydration or dissolution, and thus a type of hydrogel layer is formed on the surface of the tablets during dissolution, so that water is further prevented from infiltrating.

As means for solving these problems, PCT Application Japanese Phase Publication No. 2005-517690 has proposed a tablet that contains a solid dispersion powder obtained by spray-drying, a disintegrant, and an excipient comprising porosigen. Furthermore, Japanese Patent Application Unexamined Publication No. 5-262642/1993 has proposed a powder in which a water-soluble high molecular weight base, and if necessary, an excipient and a disintegrant are added to a poorly soluble drug. However, a concentration-enhancing polymer and a water-soluble high molecular weight base, serving as carriers, are added in large amounts, and thus the viscosity of the polymer exhibited after administration increases. Thus, the drug release from the solid dosage form is poor, so that the dissolution speed of the drug tends to be lowered.

Furthermore, in the case of a solid dispersion powder obtained by spray-drying as in PCT Application Japanese Phase Publication No. 2005-517690, it is necessary that after the solid dispersion powder is mixed with the other ingredients, the mixture is compressed and pulverized for formation of a granulated powder for tableting. The particle size of the solid dispersion powder prepared by spray-drying in this manner is small, and thus when it is simply mixed with an excipient, segregation is caused, so that the ingredients become non-uniform in the powder for tableting. Moreover, this process makes the operation complicated, and the solid dispersion may be recrystallized in compression. Furthermore, the disintegrant is added after the solid dispersion has been prepared, and thus when the solid dispersion is aggregated and bonded in the tablet due to high bonding strength of the carrier, aggregation may be formed and dispersed in water during disintegration, lowering the solubility of the drug.

Furthermore, PCT Application Japanese Phase Publication No. 2005-517690 has a simple configuration in which the solid dispersion powder is prepared in advance from a poorly soluble drug and a concentration-enhancing polymer, and then the disintegrant and the excipient are physically mixed therewith, and therefore the obtained tablet is disintegrated even in the stomach. Thus, the solid dispersion with a larger specific surface area is exposed for a long time in digestive juice, so that the solubility may be lowered due to recrystallization of the dissolved drug.

Japanese Patent Application Unexamined Publication No. 2004-67606 has proposed a tablet using fine granules obtained by: spraying a solution containing itraconazole, which is a poorly soluble drug, a water-soluble polymer, and an enteric polymer, on a mixed powder of an excipient and a disintegrant; and granulating and drying the solvent. However, due to its poor disintegration, it takes as long as 360 minutes for the drug to be dissolved from the tablet. Thus, the disintegration of the tablet is not improved.

Hirasawa et al. (Journal of the Pharmaceutical Society of Japan, 124(1), 19-23 (2004)) has proposed a tablet produced from a product obtained by: loading an ethanol dispersion liquid as a binding fluid containing nilvadipine, which is a poorly soluble drug, crospovidone, and methylcellulose, into a mixed powder of materials such as lactose, methylcellulose, and low-substituted hydroxypropylcellulose; and agitating and granulating the resultant. However, in the ethanol solution containing nilvadipine, and crospovidone and methylcellulose, serving as carriers, the components are not dissolved. Thus, it seems that the solution functions only as an agent for dispersing and diluting amorphous nilvadipine, because a co-dissolved state is not obtained. In order to disperse amorphous drug molecules in a polymer serving as a carrier, it is necessary to obtain a co-dissolved state in a cosolvent in which these components are dissolved. Thus, it seems that the solid dispersion of amorphous nilvadipine described in Journal of the Pharmaceutical Society of Japan (124(1), 19-23 (2004)) does not have sufficient solubility. Furthermore, due to the influence of the water-soluble polymer, the disintegration is suppressed, and thus it may be difficult to obtain a preparation that can be rapidly dissolved.

SUMMARY OF THE INVENTION

The present invention was completed in view of the above-described circumstances, and provides a solid dosage form comprising an enteric solid dispersion that allows a drug in the preparation to be rapidly dissolved without compromising the solubility of the solid dispersion, and a method for producing the same.

The inventors had conducted an in-depth study in order to solve the above-described problem, and found that when special low-substituted hydroxypropylcellulose is used as a disintegrant, disintegration is not lowered in tablets obtained by compression a solid dispersion, and a solid dosage form rapidly can be disintegrated and allow a drug to be dissolved. As a result, the present invention has been achieved.

More specifically, the present invention provides a solid dosage form comprising an enteric solid dispersion, the dispersion comprising a poorly soluble drug, an enteric polymer and a disintegrant wherein the disintegrant is low-substituted hydroxypropylcellulose having an average particle size of 10 to 100 µm and a specific surface area measured by BET method of at least 1.0 m$^2$/g. The solid dosage form comprising the enteric solid dispersion preferably may comprise an excipient. Moreover, the present invention provides a method for producing a solid dosage form comprising an enteric solid dispersion, the method comprising steps of: spraying an enteric polymer solution in which a poorly soluble drug has been dispersed or dissolved, on a powder of low-substituted hydroxypropylcellulose having an average particle size of 10 to 100 µm and a specific surface area measured by BET method of at least 1.0 m$^2$/g and serving as a disintegrant; and granulating the resultant; and drying.

According to the present invention, a solid dosage form with excellent solubility is obtained. The solid dosage form in the form of a granulated product as high solubility, while the solid dosage form in the form of a tablet is disintegrated within 10 minutes after introduction to an appropriate dissolution medium and can releases at least 70% by weight of a poorly soluble drug.

DETAILED DESCRIPTION OF THE PREFERRED EMBODIMENTS

Hereinafter, the present invention is described in more detail.

A poorly soluble drug used in the present invention has extremely low solubility in water, and poor absorption in ordinary oral administration. For example, the poorly soluble drug refers to a drug that is "practically insoluble or insoluble" or "very slightly soluble" as prescribed in the Japanese Pharmacopoeia Fifteenth Edition. "Solubility" of a drug in the Japanese Pharmacopoeia Fifteenth Edition refers to the degree of dissolution of the drug, powdered in the case of a solid, within 30 minutes in a solvent at 20±5° C., by shaking for 30 seconds each time at 5-minute intervals. If a drug is "practically insoluble or insoluble", then the amount of a solvent (water, in this specification) required for dissolving 1 g or 1 ml of the drug is 10,000 ml or more. If a drug is "very slightly soluble", then the amount of a solvent required for dissolving 1 g or 1 ml of the drug is 1,000 ml or more and less than 10,000 ml.

Specific examples of the poorly soluble drug used in the present invention include, but are not limited to, nifedipine, phenacetin, phenyloin, digitoxin, nilvadipine, diazepam, griseofulvin, and chloramphenicol.

In the present invention, molecules of the poorly soluble drug are dispersed in an amorphous state, and thus an enteric polymer is used as a carrier. Using an enteric polymer as a carrier of a solid dispersion is advantageous due to the dissolving properties of an enteric polymer in which drug release from the solid dosage form is suppressed in the stomach, and the drug is completely released and dissolved out of the solid dispersion after the solid dispersion has moved from the stomach to the small intestine. In other words, the drug of the solid dispersion can be specifically and efficiently dissolved and absorbed in the small intestine having the largest absorption area and the highest bioavailability of drugs in the body. This is effective also for a drug having a possibility of recrystallization after dissolution, which is regarded as a general problem of solid dispersion preparations. More specifically, when an enteric polymer is used as a carrier of a solid dispersion in a drug that may be recrystallized during a period in which the preparation moves from the stomach to the intestines, recrystallization is suppressed, and thus the solubility of the drug does not return to its original low solubility due to recrystallization, and the drug of the solid dispersion can be specifically and efficiently dissolved and absorbed in the small intestine.

According to the condition prescribed in the Japanese Pharmacopoeia Fifteenth Edition, an enteric polymer is a polymer that is "practically insoluble or insoluble (the amount of water required for dissolving 1 g or 1 ml of the drug is 10,000 ml or more)", and is dissolved in an alkaline solution. Specific examples of the enteric polymer include cellulose acetate phthalate, cellulose acetate trimellitate, cellulose acetate succinate, methylcellulose phthalate, hydroxymethylcellulose ethyl phthalate, hydroxypropylmethylcellulose phthalate, hydroxypropylmethylcellulose acetate succinate (HPMCAS), hydroxypropylmethyl acetate maleate, hydroxypropylmethyl trimellitate, carboxymethylethylcellulose, polyvinyl butyrate phthalate, polyvinyl alcohol acetate phthalate, methacrylic acid/ethyl acrylate copolymer (preferably in a weight ratio of 1:99 to 99:1), methacrylic acid/methyl methacrylate copolymer (preferably in a weight ratio of 1:99 to 99:1), and methacrylic acid copolymer. Hydroxypropylmethylcellulose phthalate, hydroxypropylmethylcellulose acetate succinate, hydroxypropylmethyl acetate maleate, and hydroxypropylmethyl trimellitate are preferable, and hydroxypropylmethylcellulose acetate succinate is particularly preferable. Moreover, among hydroxypropylmethylcellulose acetate succinate, a substance is particularly preferable that seems to allow a drug to be dissolved rapidly after the substance has moved from the stomach to the upper portion and then to the intermediate portion of the small intestine. More specifically, the polymer is preferably dissolved within 120 minutes in a phosphate buffer according to the Japanese Pharmacopoeia having a pH of 5 to 7 (5.0 to 6.8). As a factor indicating the polymer solubility of hydroxypropylmethylcellulose acetate succinate, the contents of substituents, and the composition ratio between acetyl groups and succinyl groups may be considered. Preferable examples include, but are not limited to, the following.

Specific Example 1 methoxyl group: 20 to 24% by weight, hydroxypropoxyl group; 5 to 9% by weight, acetyl group; 5 to 9% by weight, succinyl group; 14 to 18% by weight, and composition ratio; 1.5 to 3.6

Specific Example 2 methoxyl group: 21 to 25% by weight, hydroxypropoxyl group; 5 to 9% by weight, acetyl group; 7 to 11% by weight, succinyl group; 10 to 14% by weight, and composition ratio; 0.9 to 2.0

It should be noted that hydroxypropylmethylcellulose acetate succinate having substituent contents other than those listed above also can be used by combining it with Specific Examples 1 and 2, as long as this combination is dissolved within 120 minutes in a phosphate buffer having a pH of 5 to 7 (5.0 to 6.8).

The content of the enteric polymer is 1 to 75% by weight, preferably 1 to 50% by weight, and particularly preferably 1 to 35% by weight, with respect to the total amount of the solid dosage form. If the content of the enteric polymer is less than 1% by weight, then it may be difficult to obtain a completely amorphous state of the poorly soluble drug in the solid dispersion. If the content is more than 75% by weight, then the ratio of the enteric polymer in the solid dosage form becomes large, which may not be preferable in that the dose and the size of the solid dosage form become large and in that the disintegration is lowered.

The weight ratio of the enteric polymer added to the poorly soluble drug is preferably 1 to 5 when taking the poorly soluble drug as 1. If the ratio of the enteric polymer is less than 1, then the poorly soluble drug in the solid dispersion may not be in a completely amorphous state. If the ratio is more than 5, then the ratio of the enteric polymer in the solid dosage form becomes large, and thus the size of the solid dosage form becomes large, which may not be suitable for a commonly solid dosage forms.

As a solvent used when preparing the solid dispersion that contains the enteric polymer and the poorly soluble drug, a solvent is preferable in which the poorly soluble drug is well dissolved and the enteric polymer is also dissolved. Examples thereof include: methanol, ethanol, methylene chloride, and acetone; mixed solvents thereof; and solvent mixed with water. The solvent may be selected as appropriate based on the solubility of the poorly soluble drug and the enteric polymer in the solvent.

The solvent is added in an amount in which the solid concentration is preferably 3 to 18% by weight, and particularly preferably 3.5 to 12% by weight.

If necessary, surfactants such as polyethylene glycol, polyethylene oxide, propylene glycol, sucrose fatty acid ester, and glycerine fatty acid ester may be added to the ingredients of the solid dispersion as a third ingredient.

Examples of the excipient used in the present invention include lactose, cornstarch, saccharose, mannite, anhydrous calcium phosphate, crystalline cellulose, and their mixtures. It is particularly preferable to use a mixed powder containing lactose and cornstarch in a weight ratio of 7:3.

It should be noted that the content of the excipient is preferably an amount (balance) obtained by excluding the poorly soluble drug, the enteric polymer, and a disintegrant described later.

As the disintegrant of the present invention, low-substituted hydroxypropylcellulose can be used that has an average particle size of 10 to 100 μm and a specific surface area measured by the BET method of 1.0 m$^2$/g or more, because it provides granulated products with high flowability and ensures high solubility from the compressed dosage form.

The average particle size of the low-substituted hydroxypropylcellulose of the present invention may be 10 to 100 μm, and preferably approximately 20 to 60 μm. If the average particle size is less than 10 μm, then aggregability increases because the hydroxypropylcellulose is in the form of fine powder, and thus the flowability of the powder may be lowered. If the average particle size is more than 100 μm, then uniformity with the drug is lowered, and thus the product may be non-uniform. The average particle size can be measured using a HELOS&RODOS (manufactured by Sympatec) for measuring particle size distribution with laser diffractometry.

Furthermore, the specific surface area of the low-substituted hydroxypropylcellulose of the present invention may be 1.0 m$^2$/g or more. The reason for this is that if the specific surface area is less than 1.0 m$^2$/g, then high compressibility may not be obtained.

It is known that generally, higher specific surface area of a powder provides higher compressibility of the powder. The specific surface area analysis is a method for obtaining the specific surface area of a sample based on the amount of molecules adsorbed to the surface of particles of the powder at the temperature of liquid nitrogen, the molecules having adsorption occupying area that has been known. For the specific surface area analysis, the BET method can be used that is based on physical adsorption of inert gas at low temperature and low humidity. In the measurement, for example, MICROMERITICS GEMINI 2375 (manufactured by SHIMADZU CORPORATION) can be used.

Generally, specific surface area can be increased by reducing average particle size. However, as described above, if average particle size is too small, then the aggregability of a powder increases, and the flowability of the powder may be lowered. In the present invention, using compaction-grinding, a powder is provided that has high specific surface area although its average particle size is sufficient for securing the flowability of the powder.

The low-substituted hydroxypropylcellulose preferably has a bulk density of 0.30 g/ml or more.

Herein, "bulk density" refers to the bulk density in a loosely filled state, and is measured by uniformly supplying a sample from above (23 cm), through a sieve with 24 mesh according to JIS, to a cylindrical vessel (material: stainless steel) with a diameter of 5.03 cm and a height 5.03 cm (volume 100 ml), and performing weighing after leveling at the upper surface. These operations are performed using a powder tester (PT-D) manufactured by Hosokawa Micron Corporation.

The low-substituted hydroxypropylcellulose of the present invention preferably has an elastic recovery ratio of 7% or less when being subjected to compression at a compression force of 50 MPa. Accordingly, a dense molded product can be formed in a compressed state.

The elastic recovery ratio refers to an indicator of the compressibility of a powder. The elastic recovery ratio can be calculated from the following equation, based on the thickness of a tablet obtained by compression a powder in a tablet weight of 480 mg and at a compression force of 50 MPa, using a flat shape (a tableting tester (manufactured by SANKYO PIO-TECH. CO., Ltd.)) with a flat contact face for a tablet diameter of 11.3 mm.

$$\text{Elastic recovery ratio} = \{(\text{tablet thickness after 30 seconds} - \text{minimum tablet thickness})/(\text{minimum tablet thickness})\} \times 100$$

Herein, "minimum tablet thickness" refers to the lowest point obtained when the powder is compressed by an upper punch of a flat shape unit with a fixed lower punch, that is, the thickness obtained when the tablet is compressed to the extent possible. "Tablet thickness after 30 seconds" refers to the tablet thickness at 30 seconds after the upper punch is removed upward.

The swelling properties of the low-substituted hydroxypropylcellulose can be measured, for example, in the following manner: the low-substituted hydroxypropylcellulose is molded at a compression force of 1 t into a tablet having a flat face with a diameter of 15 mm; the tablet is swollen by dropping water thereonto; and the swelling properties are evaluated as the swollen volume increase ratio and the swollen volume increase rate at that time. When alkali cellulose is used in which the weight ratio of sodium hydroxide with respect to anhydrous cellulose is 0.1 to 0.3, the swollen volume increase ratio is preferably 300% or more, and the swollen volume increase rate is preferably 100%/min or more.

The swollen volume increase ratio can be obtained in the following manner: the powder is compressed at a compression force of 1 t into a tablet having a flat face with a diameter of 15 mm; a punch with a pipe is attached instead of the upper punch; the tablet is caused to absorb water for 10 minutes by dropping water through this pipe onto the tablet contained in a mortar; and the swollen volume increase ratio is obtained at that time. The water is dropped at a rate of 1 ml/min for 10 minutes. The increase in the volume can be calculated from the following equation, based on a change in the thickness of the tablet.

$$\text{Swollen volume increase ratio} = (\text{difference in tablet thickness between before and after adding water} / \text{tablet thickness before adding water}) \times 100$$

It should be noted that in the equation above, "difference in tablet thickness between before and after adding water" refers to a value obtained by subtracting the tablet thickness before adding water from the tablet thickness after adding water for 10 minutes.

Furthermore, the swollen volume increase ratio of the low-substituted hydroxypropylcellulose powder is preferably 300% or more in view of swelling properties, which are important properties as the disintegrant. If the swollen volume increase ratio is less than 300%, then the disintegration time of a preparation produced from the powder may be longer.

The swollen volume increase rate refers to an initial swelling ratio at 30 seconds after starting the addition of water, when the swollen volume increase ratio is measured under the same condition as the above-described method, and can be calculated from the following equation.

$$\text{Swollen volume increase rate} = (\text{difference in tablet thickness before and after initially adding water} / \text{tablet thickness before adding water}) \times 100 / 0.5$$

In the equation above, "difference in tablet thickness before and after initially adding water" refers to a value obtained by subtracting the tablet thickness before adding water from the tablet thickness at 30 seconds after starting the addition of water.

The swollen volume increase rate of the low-substituted hydroxypropylcellulose powder of the present invention is preferably 100%/min or more in view of swelling properties, which are important properties as the disintegrant. If the swollen volume increase rate is less than 100%/min, then the disintegration time of a preparation produced from the powder may be longer.

The low-substituted hydroxypropylcellulose of the present invention is a powder having high flowability and preferably having a repose angle of 42° or less, the repose angle being one type of indicators of the flowability of a powder. The repose angle refers to an angle formed by a horizontal plane and a generatrix of a corn that is a deposition formed by dropping the sample onto the plane. For example, using a powder tester PT-D (manufactured by Hosokawa Micron Corporation), the repose angle can be calculated by allowing the sample to flow from a height of 75 mm onto a disc-shaped metal stage having a diameter of 80 mm, until a constant angle is obtained, and then measuring the angle formed by the deposited powder and the stage. The smaller this angle is, the better the flowability of the powder is.

As described in Japanese Patent Application No. 2006-215401, the low-substituted hydroxypropylcellulose of the present invention can be obtained in the following manner: an aqueous sodium hydroxide solution is added and mixed with powdered pulp, and thus alkali cellulose is produced in which the weight ratio of sodium hydroxide with respect to anhydrous cellulose is 0.1 to 0.3; the alkali cellulose is etherified; the sodium hydroxide is neutralized after performing or without performing a dissolution step; the resultant is washed and dried; and then the dried product is compaction-ground in a pulverization step.

More specifically, a method for producing a low-substituted hydroxypropylcellulose powder may comprise the steps of: (1) adding an aqueous sodium hydroxide solution to powdered pulp such that the weight ratio of sodium hydroxide with respect to anhydrous cellulose is 0.1 to 0.3 so as to producing alkali cellulose; (2) etherifying the obtained alkali cellulose so as to obtain a crude reaction product; (3) neutralizing the sodium hydroxide contained in the obtained crude reaction product; (4) washing and dehydrating the resultant; (5) drying the resultant; and (6) pulverizing by compaction-grinding. Furthermore, a method for producing a low-substituted hydroxypropylcellulose powder that has a number of moles substituted per anhydrous glucose unit of 0.05 to 1.0, that is insoluble in water, and that is swollen by absorbing water, comprises the steps of: (1) adding an aqueous sodium hydroxide solution to powdered pulp such that the weight ratio of sodium hydroxide with respect to anhydrous cellulose is 0.1 to 0.3 so as to produce alkali cellulose; (2) etherifying the obtained alkali cellulose so as to obtain a crude reaction product; (3) neutralizing the sodium hydroxide contained in the obtained crude reaction product without performing a dissolution step of dissolving part or whole of the crude reaction product; (4) washing and dehydrating the resultant; (5) drying the resultant; and (6) pulverizing by compaction-grinding. In the wash and dehydration step, the resultant is preferably washed and dehydrated such that the water content is 65% by weight or less.

First, any pulverization method may be applied for obtaining powdered pulp that is used as a raw material. The average particle size thereof is preferably 60 to 300 μm. It is inefficient from an industrial viewpoint to prepare powdered pulp having an average particle size of less than 60 μm. If the average particle size is more than 300 μm, then the uniformity with the aqueous sodium hydroxide solution may be poor.

The step of producing alkali cellulose is preferably performed by dropping or spraying the aqueous sodium hydroxide solution to the powdered pulp and mixing the resultant. At that time, the sodium hydroxide acts as a catalyst in the etherification. The alkali cellulose may be produced preferably by using either a method in which mixing is performed in an internally-agitating type reaction device, and then etherification is successively performed, or a method in which alkali cellulose prepared in another mixing device is charged into a reaction device, and etherification is performed.

Furthermore, it was found that the amount of the sodium hydroxide in the alkali cellulose affects not only the reaction efficiency but also the swelling properties and the compressibility of final products. The optimum amount of the sodium hydroxide in the alkali cellulose may be 0.1 to 0.3 in the weight ratio of the sodium hydroxide with respect to anhydrous cellulose (referring to the balance obtained by removing water from the pulp). If the amount is less than 0.1, then the swelling properties, in particular, the volume increase ratio when the product is swollen by absorbing water may be lowered, the disintegration may be lowered, and the compressibility also may be lowered. Furthermore, if the amount is more than 0.3, then the swollen volume increase ratio and the swollen volume increase rate when absorbing water (described later) may be lowered, and the compressibility also may be lowered.

The sodium hydroxide is preferably added as an aqueous 20 to 40% by weight solution.

The following etherification step is performed by charging the alkali cellulose into a reaction device, performing nitrogen purge, and then charging propylene oxide into the reaction device as an etherifying agent, thereby causing a reaction. The ratio of the propylene oxide charged is preferably approximately 0.1 to 1.0 mole with respect to 1 mole of anhydrous glucose units. The reaction temperature is approximately 40 to 80° C., and the reaction time is approximately 1 to 5 hours.

It should be noted that after the etherification step, a dissolution step may be performed, if necessary. The dissolution step is performed by dissolving part or whole of the crude reaction product after the etherification in water or hot water. The amount of water or hot water used varies depending on the amount of the crude reaction product to be dissolved, but the amount of water for dissolving whole of the crude reaction product is usually 0.5 to 10 in the weight ratio with respect to the low-substituted hydroxypropylcellulose in the crude reaction product.

In order to further improve the load in the wash and dehydration step described later, and the compressibility of low-substituted cellulose ether, it is preferable not to perform the dissolution step.

In the following neutralization step, since the sodium hydroxide used as the catalyst remains in the reaction product, neutralization is preferably performed by loading the crude reaction product into water or hot water containing acids in an amount equivalent to the sodium hydroxide. Alternatively, neutralization may be performed by adding water or hot water containing the equivalent amount of acids to the reaction product.

Examples of the acids that are used herein include mineral acids such as hydrochloric acid, sulfuric acid, and nitric acid, and organic acids such as formic acid and acetic acid.

In the following wash and dehydration step, while washing the obtained neutralized product preferably using water or hot water, dehydration is performed by a method preferably selected from centrifugation, suction filtration, and pressure filtration, for example. The low-substituted hydroxypropylcellulose in an obtained dehydrated product cake is in the form of fibers as in the raw material pulp. The dehydrated product obtained after performing the dissolution step has a dehydration ratio of approximately 70 to 90% by weight, although this ratio depends on the number of moles substituted. The dehydration ratio of the dehydrated product obtained without performing the dissolution step is usually 65% by weight or less, so that the load in the following drying step can be reduced, and the productivity is improved. Furthermore, it is advantageous in that the steps can be simplified because the dissolution step is not included.

Furthermore, in view of the compressibility of the product, when a fibrous substance is pulverized, the obtained product has higher specific surface area and thus higher compressibility.

The drying step of drying the obtained dehydrated product is preferably performed using a drier such as a fluidized bed drier or a drum drier at 60 to 120° C.

The pulverization step may be performed by compaction-grinding the dried product obtained by the above-described method.

For this compaction-grinding, a pulverizer such as a roller mill, a ball mill, a bead mill, or a millstone mill can be used. In a roller mill, with a centrifugal force or gravity load accompanying its rotational movement, rollers or balls roll over while compressing/shearing a pulverization target on a mill wall. Examples thereof include an IS mill manufactured by Ishikawajima-Harima Heavy Industries Co., Ltd., a VX mill manufactured by Kurimoto, Ltd., and an MS roller mill manufactured by MASUNO SEISAKUSHO LTD. A ball mill uses, as a milling medium, steel balls, magnetic balls, cobbled stones, or the like. Examples thereof include a ball mill manufactured by KURIMOTO TEKKO KK, a tube mill manufactured by Otsuka Iron Works, and a planetary ball mill manufactured by FRITSCH. A bead mill is similar to the ball mill, but is different therefrom in that the diameter of balls used is smaller and in that acceleration of the balls can be further increased by rotating the internal portion of the device at high speed. Examples thereof include a bead mill manufactured by Ashizawa. A millstone mill can grind a powder by rotating a millstone at narrow clearance at high speed. Examples thereof include Serendipiter manufactured by MASUKO SANGYO CO., LTD.

The roller mill is particularly preferable because it reduces foreign metal substances mixed in, requires small installation area, and provides high productivity.

When fibrous particles serving as a pulverization raw material are repeatedly compaction-ground, the fibrous and hollow tubular form derived from the raw material pulp is lost, and thus primary particles can be made smaller, so that the specific surface area is increased. Also, since the fibrous form derived from the raw material pulp is lost, a powder having uniform particle shape can be obtained.

It has been considered that the compressibility of low-substituted hydroxypropylcellulose produced by conventional impact pulverization is exerted by intertwining of fibrous substances. When fibrous particles are increased based on this idea for improving the compressibility, the flowability is lowered. However, a low-substituted hydroxypropylcellulose powder produced by compaction-grinding exhibits surprisingly high compressibility, although the fibrous form has been lost due to the compaction-grinding.

Next, preferably, the pulverized product is sieved following the usual method, and thus the targeted low-substituted hydroxypropylcellulose powder can be obtained. The opening of a sieve herein may be approximately 38 to 180 μm.

The thus obtained low-substituted hydroxypropylcellulose powder has high flowability, excellent compressibility, and excellent swelling properties, regardless of the fibrous form derived from raw material pulp. Furthermore, due to its excellent compressibility and excellent disintegration, the amount of this powder added to a tablet can be reduced, and thus the size of the tablet can be made smaller. Moreover, the molding pressure in production of the tablet can be made lower, which provides the advantage of being able to reduce physical influences such as recrystallization of the solid dispersion during process.

In the present invention, in addition to the low-substituted hydroxypropylcellulose, for example, carmellose, carmellose sodium, carmellose calcium, croscarmellose sodium, low-substituted hydroxypropylcellulose (L-HPC) having 5 to 16% by weight of hydroxypropoxyl groups, hydroxypropyl starch, sodium carboxymethyl starch, crospovidone, and their mixtures can be used.

The content of the disintegrant is preferably 1 to 98% by weight, and more preferably 1 to 60% by weight, with respect to the total amount of the solid dosage form. If the content of the disintegrant is less than 1% by weight, then it may be difficult to disintegrate the solid dosage form because the amount of the disintegrant is small. If the content is more than 98% by weight, then an effective amount of drug may not be contained.

In the solid dosage form of the present invention, the granulated product refers to a powder and a granule prescribed in the Japanese Pharmacopoeia Fifteenth Edition.

In a case where the solid dosage form is in the form of a tablet, a lubricant may be added, if necessary. Examples of the lubricant include magnesium stearate, sucrose fatty acid ester, polyethylene glycol, talc, and stearic acid.

In a case where the lubricant is added, the amount of the lubricant added is preferably 0.5 to 2% by weight with respect to the total amount of the dosage form excluding the lubricant. If the amount of the lubricant added is less than 0.5% by weight, then sufficient lubricative properties may not be obtained, so that the preparation adheres to a mortar or a punch during tableting. If the amount is more than 2% by weight, then the hardness may decrease and the disintegration may be lowered.

The tablet obtained in the present invention is not completely disintegrated in an acidic environment in the stomach. In a neutral to alkaline environment in the intestine, the tablet is disintegrated, and the solubility of the drug is improved. The reason for this is that when the granulated product as a powder for tableting is prepared, the enteric polymer serving as the carrier is sprayed on and attached to the surface of the disintegrant. In the tablet using these granulated product, disintegration of the tablet is suppressed in the stomach in which water hardly permeates the internal portion of the tablet, and the tablet starts to be disintegrated in the intestines in which the carrier starts to be dissolved, enabling water to permeate and the disintegrant to swell. As a result, the surface area of particles of the solid dispersion is increased, and thus the solubility is improved.

Next, a method for producing a solid dosage form and a tablet of the enteric solid dispersion according to the present invention is described.

In a case where the enteric solid dosage form of the solid dispersion of the present invention is a granulated product, the granulated product is obtained preferably by: spraying an enteric polymer solution in which the poorly soluble drug has been dispersed or dissolved, on a mixed powder of the excipient and the disintegrant; and granulating and then drying the resultant. More specifically, in a state where the mixed powder of the excipient and the disintegrant is allowed to flow in a granulating device, the enteric polymer solution prepared in advance in which the poorly soluble drug has been dispersed or dissolved is sprayed on the mixed powder, the resultant is granulated and dried, and then the particle size is regulated.

Examples of the granulating device include a fluidized bed granulating device, a high-speed agitation granulating device, a rolling granulating device, and a dry granulating device. The fluidized bed granulating device is particularly preferable because it does not apply mechanical shear to the granulated product.

There is no particular limitation on the method for producing the enteric solid dosage form of the solid dispersion of the present invention, except that a low-substituted hydroxypropylcellulose having an average particle size of 10 to 100 μm, and a specific surface area measured by the BET method of 1.0 m$^2$/g or more is used as the disintegrant. For example, the following method can be used.

The enteric polymer is completely dissolved in the above-described solvent such as ethanol or water, and then the poorly soluble drug is loaded thereinto, and thus the solid dispersion solution is obtained. Herein, it is possible to load ingredients constituting the solid dispersion solution into the solvent at a time, but it is preferable to dissolve the enteric polymer first in order to achieve the stability of the drug in the finally obtained solid dosage form and to shorten the dissolution time of the poorly soluble drug. There is no particular limitation on the concentration of the solid dispersion solution, but the concentration is preferably 400 mPa·s or less, and particularly preferably 100 mPa·s or less, because the solution is to be sprayed.

While the mixture of these various ingredients such as the disintegrant is allowed to flow, for example, in the fluidized bed granulating device, the solid dispersion solution is sprayed thereon, and the resultant is granulated and dried, and thus the granulated product can be obtained. In the spray/granulation step, the inlet air temperature is preferably 150° C. or lower, and particularly preferably 100° C. or lower, considering a case in which an organic solvent is used.

The exhaust air temperature is preferably 30° C. or higher, and particularly preferably 40° C. or higher. The spray rate is preferably 50 g/min or less, and particularly preferably 30 g/min or less. The spray air pressure is preferably 250 kPa or less, and particularly preferably 200 kPa or less. Furthermore, after the spraying, in the drying step performed in order not to leave the solvent in the obtained granulated product, the inlet air temperature is preferably 150° C. or lower, and particularly preferably 100° C. or lower, and the drying time is preferably 10 to 60 minutes.

The obtained granulated product can be used as it is. However, the obtained granulated product can be, for example, sieved or pulverized for obtaining a solid dosage form having more uniform particle size distribution. For example, the particle size may be regulated with a sieve with an opening of 500 μm, for example.

On the other hand, in a case where the solid dosage form of the solid dispersion is a tablet, the tablet may be obtained by performing compression in a tableting machine, using the granulated product obtained by the above-described method as a powder for tableting, and adding an excipient, a disintegrant, or a lubricant thereto, if necessary.

For the tableting, for example, a rotary tableting machine, or a single tableting machine may be used. However, there is no limitation to this, and a specially customized tableting machine also may be used. The molding pressure during tableting is 1 to 130 kg/cm², and particularly preferably 10 to 100 kg/cm².

When the thus obtained granulated product of the enteric solid dispersion is evaluated following "Dissolution Test" described in the Japanese Pharmacopoeia Fifteenth Edition using the 2nd fluid (artificial intestinal juice) according to the Japanese Pharmacopoeia having a pH of 6.8, the concentration of the drug dissolved within 5 minutes after administration is 70% or more with respect to the amount administered, that is, high solubility is exhibited. Furthermore, the dissolution rate of the drug in the 1st fluid (artificial gastric juice) according to the Japanese Pharmacopoeia having a pH of 1.2 is 10 wt % or less of the initial concentration of the drug administered even after two hours, that is, the granules are not disintegrated in the stomach.

When the obtained tablet of the enteric solid dispersion is evaluated following "Disintegration Test" described in the Japanese Pharmacopoeia Fifteenth Edition using the 2nd fluid (artificial intestinal juice) according to the Japanese Pharmacopoeia having a pH of 6.8, the tablets are disintegrated within 10 minutes after administration, and when the tablets are evaluated following "Dissolution Test" described in the Japanese Pharmacopoeia Fifteenth Edition using the 2nd fluid (artificial intestinal juice) according to the Japanese Pharmacopoeia having a pH of 6.8, the concentration of the drug dissolved within 10 minutes after administration is 70% or more with respect to the amount administered, that is, high disintegration and high solubility are exhibited. Furthermore, the disintegration time is more than 15 minutes in the 1st fluid according to the Japanese Pharmacopoeia, that is, the tablets are not disintegrated in the stomach.

The solid dosage form obtained in the present invention may be coated by known methods in order to provide taste-masking or odor-masking, to make the preparation enteric, or to achieve slow release of the preparation. Examples of the coating agent used at that time include: water-soluble polymers, for example, alkylcellulose such as methylcellulose, hydroxyalkylcellulose such as hydroxyethylcellulose and hydroxypropylcellulose, hydroxyalkylalkylcellulose such as hydroxyethylmethylcellulose and hydroxypropylmethylcellulose, polyvinyl alcohol, polyvinyl pyrrolidone; enteric polymers such as cellulose acetate phthalate, methacrylic acid copolymer L, methacrylic acid copolymer LD, methacrylic acid copolymer S, hydroxypropylmethylcellulose phthalate, hydroxypropylmethylcellulose acetate succinate, and carboxymethylethylcellulose; and stomach-soluble polymers such as polyvinyl acetal diethylaminoacetate and aminoalkyl methacrylate copolymer.

EXAMPLES

Hereinafter, the present invention is specifically described by way of examples and comparative examples, but the present invention is not limited to these examples.

Synthesis Examples 1 to 3

Synthesis of the Low-Substituted Hydroxypropylcellulose Powder

First, 806 g of powdered pulp (750 g in an anhydrous state) was charged into a 10 L internally-agitating type reaction device, 303 g of 26% by weight sodium hydroxide solution was charged into the reaction device, then mixing was performed at 45° C. for 30 minutes, and thus alkali cellulose was obtained in which the weight ratio of sodium hydroxide with respect to anhydrous cellulose was 0.105. Next, nitrogen purge was performed, 123 g of propylene oxide (0.164 parts by weight with respect to cellulose) was added to the resultant, then the mixture was reacted at a jacket temperature of 60° C. for 1.5 hours, and thus 1232 g of hydroxypropylcellulose crude reaction product was obtained in which the number of moles substituted with hydroxypropoxyl groups per anhydrous glucose unit was 0.28. The etherification efficiency was 61.4%.

Next, 236 g of 50% by weight acetic acid was added and mixed in the 10 L internally-agitating type reaction device, thereby performing neutralization. The neutralized product was washed in hot water at 90° C. and dehydrated, using a batch-type centrifuge at a rotational speed of 3000 rpm. The water content of the dehydrated product was 58.2% by weight. The dehydrated product was dried at 80° C. for one whole day and night in a shelf drier.

The dried product was pulverized using a batch-type planetary ball mill P-5 manufactured by FRITSH, at 255 rpm for 60 minutes. The obtained pulverized product was sieved through sieves with openings of 38, 75, and 180 μm, and thus the low-substituted hydroxypropylcellulose powders (Samples 1 to 3, respectively) having a hydroxypropoxyl group content of 10.9% by weight were obtained. These powders were evaluated by the above-described method, in terms of average particle size, specific surface area, bulk density, repose angle, elastic recovery ratio, compressibility, swollen volume increase ratio, and swollen volume increase rate. Table 1 shows the evaluation results.

TABLE 1

| | evalution results of powder properties | | | | | | | |
|---|---|---|---|---|---|---|---|---|
| | average particle size (μm) | specific surface area (m²/g) | bulk desity (g/mL) | flowablity repose angle (°) | elatic recovery ratio (%) | compressibility tablet hardness (kgf) | swollen volume increase ratio (%) | swollen volume increase rate (%/min) |
| Sample 1 | 24 | 1.25 | 0.45 | 38 | 3.5 | 45 | 302 | 175 |
| Sample 2 | 42 | 1.21 | 0.42 | 37 | 3.8 | 42 | 330 | 190 |
| Sample 3 | 57 | 1.08 | 0.41 | 37 | 4.5 | 40 | 401 | 200 |

Examples 1 to 3 and Comparative Example 1

Solid dispersion solutions were prepared by dissolving predetermined amounts (listed in Table 2) of nifedipine and hydroxypropylmethylcellulose acetate succinate (HPM-CAS), which is an enteric polymer, in a mixed solvent containing ethanol and water in a weight ratio of 8:2. Then, in a state where a mixture of predetermined amounts (listed in Table 2) of low-substituted hydroxypropylcellulose (L-HPC), lactose (Pharmatose manufactured by DMV International), and cornstarch (cornstarch W manufactured by NIHON SHOKUHIN KAKO) was allowed to flow in a fluidized bed granulating device (Multiplex MP-01 manufactured by POWREX CORPORATION), the solid dispersion solutions were sprayed on the mixture, the resultants were granulated and dried, the particle size was regulated with a sieve of 30 mesh (opening 500 μm), and thus granulated products were obtained. The granulating and drying conditions at that time are as below.

Inlet air temperature: 60° C.,
Exhaust air temperature: 40° C.;
Spray rate: 10 g/min,
spray air pressure: 200 kPa;
Inlet air temperature in drying step: 75° C.,
drying time: 15 minutes.

Comparative Example 1

A granulated product was produced as in Example 1, except that powders excluding the low-substituted hydroxypropylcellulose in Example 1 were prepared in the composition in Table 2.

Comparative Example 2

A granulated product was produced as in Example 1, except that low-substituted hydroxypropylcellulose (L-HPC) (hydroxypropoxyl group 10.9% by weight, average particle size 44 μm, specific surface area 0.92 m²/g, bulk density 0.44 g/ml, repose angle 39°, elastic recovery ratio 3.8%, swollen volume increase ratio 250%, swollen volume increase rate 200%/min) was used instead of the low-substituted hydroxypropylcellulose in Example 1.

Table 2 shows results obtained by observing the granulated products of the respective formulae, in terms of a flowing state of the granulated products in the granulating step. In the evaluation of a flowing state, if the flowing state is "Excellent", then the flowability is particularly good. If the flowing state is "Good", then the flowability is good. If the flowing state is "Poor", then the flowability is comparatively poor, and there are indications that blocking (referring to a state in which powder is retained and does not flow in layers) occurs in layers. If the flowing state is "Disable", then the fluid is blocked in layers and cannot flow.

As shown in Table 2, the granulated products in Examples 1 to 3 using Samples 1 to 3 were excellent in flowability, but the flowability of the granulated product in Comparative Example 1 was inferior to those of Examples 1 to 3. Furthermore, in Comparative Example 2, the flowability of the granulated powder was lowered during process, and blocking occurred in layers, so that it was impossible to complete granulation.

TABLE 2

| | composition | | | | | | |
|---|---|---|---|---|---|---|---|
| | nifedipine (g) | HPMCAS *1 (g) | L-HPC (g) | lactose (g) | corn starch (g) | total (g) | flowability |
| Example 1 | 12 | 24 | 144 *2 | 42 | 18 | 240 | excellent |
| Example 2 | 12 | 24 | 144 *3 | 42 | 18 | 240 | excellent |
| Example 3 | 12 | 24 | 144 *4 | 42 | 18 | 240 | excellent |
| Comp. Ex. 1 | 12 | 24 | — | 142.8 | 61.2 | 240 | good |
| Comp. Ex. 2 | 12 | 24 | 144 | 42 | 18 | 240 | not flow |

*1 HPMCAS having 7.4 wt % hydroxypropoxyl groups, 23 wt % methoxyl groups, 9.3 wt % acetyl groups and 11.0 wt % succinyl group was used.
*2 L-HPC of Sample 1 was used.
*3 L-HPC of Sample 2 was used.
*4 L-HPC of Sample 3 was used.

<Drug Solubility of Examples 1 to 3 and Comparative Examples 1 and 2>

The granulated products obtained in Examples 1 to 3 and Comparative Examples 1 and 2 were tested in an amount of 1800 mg (containing 90 mg of nifedipine) following Paddle method of Dissolution Test in the Japanese Pharmacopoeia Fifteenth Edition. As the conditions for Dissolution Test, the rotational speed was set to 100 rpm, and 900 ml of the 2nd fluid (pH 6.8) according to the Japanese Pharmacopoeia was used as a test fluid. For the sake of reference, 90 mg of nifedipine bulk powder was also tested in a similar manner. Table 3 shows the results.

Herein, in the granulated product of Comparative Example 2, blocking occurred during fluidized bed granulation. Accordingly, it was difficult to continuously perform good granulation, and thus it was impossible to perform Dissolution Test.

In a case where all granulated products in Example 2 were evaluated in "Dissolution Test" described in the Japanese Pharmacopoeia Fifteenth Edition, using the 1st fluid (artificial gastric juice, pH 1.2) according to the Japanese Pharmacopoeia, the dissolution rate after 120 minutes was 10% or less of the initial concentration of the drug administered. In a case where evaluation was performed in "Dissolution Test" described in the Japanese Pharmacopoeia Fifteenth Edition, using the 2nd fluid (artificial intestinal juice, pH 6.8) according to the Japanese Pharmacopoeia, the dissolution rate within 10 minutes was 70% or more. More specifically, the solubility of the drug was improved more than in Comparative Example 1 in which the low-substituted hydroxypropylcellulose serving as the disintegrant was not added. Furthermore, in Dissolution Test using the 2nd fluid according to the Japanese Pharmacopoeia, the concentration and rate of the drug dissolved were significantly high compared with the solubility of the nifedipine bulk powder.

In the evaluation above, it has been confirmed that the granulated products of the solid dispersions of the present invention allow the drug to be dissolved rapidly and at high rate.

TABLE 3

| time (minutes) | dissolution percentage of drug (%)/ Japanese Pharmacopoeia 2nd fluid | | | | | | | JP 1st fluid |
|---|---|---|---|---|---|---|---|---|
| | 0 | 2 | 5 | 10 | 15 | 20 | 30 | 120 |
| Example 1 | 0 | 100 | 100 | 100 | 97.1 | 90 | 76 | 10% or less |
| Example 2 | 0 | 100 | 100 | 96.1 | 86 | 77.6 | 70.8 | 10% or less |
| Example 3 | 0 | 100 | 100 | 98.3 | 84.5 | 78.3 | 70.7 | 10% or less |
| Comp. Ex. 1 | 0 | 47.2 | 57.1 | 61.3 | 59.6 | 58.8 | 54.6 | 10% or less |
| Com. Ex. 2 | not measurable because of granulation was impossible | | | | | | | |
| nifedipine alone | 0 | 0.6 | 3.4 | 9.3 | 10 | 10.6 | 11.9 | |

Examples 4 to 6 and Comparative Example 3

Using the granulated products prepared in Examples 1 to 3 as powders for tableting, 201 mg of tablets were produced (Examples 4 to 6) by adding 0.5% by weight of magnesium stearate as a lubricant to the powders for tableting, mixing the resultants, and processing the mixtures in a rotary tableting machine (Vergo manufactured by Kikusui Seisakusho Ltd.) at a molding pressure of 20 kg/cm$^2$. As a comparative example, using a granulated product prepared in Comparative Example 1 as a powder for tableting, a tablet was produced (Comparative Example 3) as in Example 4. The obtained tablets were tested in terms of hardness, and drug dissolution in the 1st or 2nd fluid according to the Japanese Pharmacopoeia. Table 4 shows the results.

The tablets obtained in Examples 4 to 6 exhibited appropriate hardness and excellent disintegration (the 2nd fluid according to the Japanese Pharmacopoeia).

On the other hand, in a case where the low-substituted hydroxypropylcellulose serving as the disintegrant was not added (Comparative Example 3), good hardness and good disintegration (the 2nd fluid according to the Japanese Pharmacopoeia) were exhibited, but the disintegration time in the 1st fluid according to the Japanese Pharmacopoeia was 15 minutes or less.

<Drug Solubility of Examples 4 to 6 and Comparative Example 3>

Dissolution Test as in Examples 1 to 3 was performed on 1890 mg of the tablets (containing 90 mg of nifedipine) obtained in Examples 4 to 6 and Comparative Example 3. Furthermore, for the sake of reference, 90 mg of nifedipine bulk powder was also tested in a similar manner. Table 5 shows the results.

In the tablets obtained in Examples 4 to 6, the dissolution rate was by no means inferior to that from the granulated products. On the other hand, in the tablet obtained in Comparative Example 3, the solubility was not substantially improved.

In the tablets obtained in Examples 4 to 6, the rate of the drug dissolved after 120 minutes in the 1st fluid according to the Japanese Pharmacopoeia was 10% or less of the initial concentration of the drug administered. Furthermore, the dissolution rate within 10 minutes in the 2nd fluid according to the Japanese Pharmacopoeia was 70% or more. More specifically, the drug was dissolved in an excellent manner. Furthermore, in Dissolution Test using the 2nd fluid according to the Japanese Pharmacopoeia, the concentration and rate of the drug dissolved were significantly high compared with the solubility of the nifedipine bulk powder.

On the other hand, in a case where the low-substituted hydroxypropylcellulose serving as the disintegrant was not added, the rate of the drug dissolved after 120 minutes in the 1st fluid (artificial gastric juice) according to the Japanese Pharmacopoeia was 10% or less of the initial concentration of the drug administered, but the dissolution rate within 10 minutes in the 2nd fluid according to the Japanese Pharmacopoeia was less than 70%, that is, the solubility was not improved.

In the evaluation above, it has been confirmed that the tablets of the solid dispersions of the present invention have excellent disintegration, and allow the drug to be dissolved rapidly and at high rate.

TABLE 5

| time (minutes) | dissolution perentage of drug (%)/ Japanese Pharmacopoeia 2nd fluid | | | | | | | JP 1st fluid |
|---|---|---|---|---|---|---|---|---|
| | 0 | 2 | 5 | 10 | 15 | 20 | 30 | 120 |
| Example 4 | 0 | 71 | 85.8 | 91.7 | 93.1 | 84.3 | 84.3 | 10% or less |
| Example 5 | 0 | 65.3 | 86.8 | 93 | 94.5 | 94.5 | 88.4 | 10% or less |
| Example 6 | 0 | 86 | 90.6 | 89.1 | 82.9 | 82.9 | 72.2 | 10% or less |
| Comp. Ex. 3 | 0 | 47.2 | 57.1 | 61.3 | 59.6 | 58.8 | 54.6 | 10% or less |
| nifedipine alone | 0 | 0.6 | 3.4 | 9.3 | 10 | 10.6 | 11.9 | |

TABLE 4

| | composition per tablet | | | | | | | tablet | disintegration time | |
|---|---|---|---|---|---|---|---|---|---|---|
| | nifedipine (mg) | HPMCAS *1 (mg) | L-HPC (mg) | lactose (mg) | corn starch (mg) | St-Mg (mg) | total (mg) | hardness (kgf) | JP 2nd fluid (min) | JP 1st fluid (min) |
| Example 4 | 10 | 20 | 120 *2 | 35 | 15 | 1 | 201 | 5.2 | 26 | >30 |
| Example 5 | 10 | 20 | 120 *3 | 35 | 15 | 1 | 201 | 7.3 | 4.5 | >30 |
| Example 6 | 10 | 20 | 120 *4 | 35 | 15 | 1 | 201 | 6.3 | 9.8 | >30 |
| Comp. Ex. 3 | 10 | 20 | — | 119 | 51 | 1 | 201 | 26 | >30 | 10.5 |

*1 HPMCAS having 7.4 wt % hydroxypropoxyl groups, 23 wt % methoxyl groups, 9.3 wt % acetyl groups and 11.0 wt % succinyl groups was used.
*2 L-HPC of Sample 1 was used.
*3 L-HPC of Sample 2 was used.
*4 L-HPC of Sample 3 was used.

Examples 7 to 13

Granulated products were obtained as in Examples 1 to 3, using predetermined amounts (listed in Table 6) of nifedipine, hydroxypropylmethylcellulose (HPMC), lactose (Pharmatose manufactured by DMV International), and cornstarch (cornstarch W manufactured by NIHON SHOKUHIN KAKO), in the mixing ratios in Table 6.

Example 14

A granulated product was obtained as in Examples 1 to 3, in the mixing ratio in Table 6, except that the degree of substitution of the hydroxypropylmethylcellulose acetate succinate was changed.

Examples 15 and 16

Granulated products of solid dispersions were obtained as in Examples 1 to 3, in the mixing ratios in Table 6, except that hydroxypropylmethylcellulose phthalate was used instead of the hydroxypropylmethylcellulose acetate succinate in Example 1.

Comparative Examples 4 and 5

Granulated products of solid dispersions were obtained as in Examples 1 to 3, in the mixing ratios in Table 6, except that the low-substituted hydroxypropylcellulose in Comparative Example 2 was used.

Table 6 shows results obtained by observing the granulated products of the respective formulae, in terms of a flowing state of the granulated products in the granulating step.

The granulated products in Examples 7 to 16 were excellent in flowability, but the flowability of the granulated product in Comparative Example 4 was inferior to those of Examples 7 to 16. Furthermore, in Comparative Example 5, the flowability during the granulation was lowered, and blocking occurred in layers, so that it was impossible to complete the granulation.

<Drug Solubility of Examples 7 to 16 and Comparative Examples 4 to 5>

The granulated products obtained in Examples 7 to 16 and Comparative Example 5 in an amount of 1800 mg (containing 90 mg of nifedipine) were evaluated as in Examples 1 to 3. Table 7 shows the results.

In a case where all granulated products in Examples 7 to 16 were evaluated in "Dissolution Test" described in the Japanese Pharmacopoeia Fifteenth Edition, using the 1st fluid (artificial gastric juice, pH 1.2) according to the Japanese Pharmacopoeia, the dissolution rate after 120 minutes was 10% or less of the initial concentration of the drug administered. In a case where evaluation was performed in "Dissolution Test" described in the Japanese Pharmacopoeia Fifteenth Edition, using the 2nd fluid (artificial intestinal, juice, pH 6.8) according to the Japanese Pharmacopoeia, the dissolution rate within 10 minutes was 70% or more. More specifically, the solubility of the drug was improved more than in Comparative Example 4 in which the low-substituted hydroxypropylcellulose was added. Furthermore, in Dissolution Test using the 2nd fluid according to the Japanese Pharmacopoeia, the concentration and rate of the drug dissolved were significantly high compared with the solubility of the nifedipine bulk powder.

TABLE 7

| time (minutes) | dissoluton percentage (%)/ Japanese Pharmacopoeia 2nd fluid | | | | | | | JP 1st fluid |
|---|---|---|---|---|---|---|---|---|
|  | 0 | 2 | 5 | 10 | 15 | 20 | 30 | 120 |
| Example 7 | 0 | 100 | 100 | 100 | 100 | 100 | 94.4 | 10% or less |
| Example 8 | 0 | 100 | 100 | 100 | 91.5 | 85.9 | 74.6 | 10% or less |
| Example 9 | 0 | 100 | 89.1 | 72.2 | 64.5 | 58.4 | 55.3 | 10% or less |
| Example 10 | 0 | 100 | 93.7 | 73.7 | 64.5 | 59.9 | 53.8 | 10% or less |
| Example 11 | 0 | 98.6 | 100 | 100 | 97.3 | 89.1 | 78.1 | 10% or less |
| Example 12 | 0 | 100 | 100 | 99.8 | 92.2 | 82.9 | 73.7 | 10% or less |

TABLE 6

| | composition | | | | | | | |
|---|---|---|---|---|---|---|---|---|
| | nifedipine (g) | HPMCAS (g) | HPMCP (g) | L-HPC (g) | lactose (g) | corn starch (g) | total (g) | flowability |
| Example 7 | 12 | 24 *1 | | 24 *4 | 126 | 54 | 240 | excellent |
| Example 8 | 12 | 24 *1 | | 96 *4 | 75.6 | 32.4 | 240 | excellent |
| Example 9 | 6 | 12 *1 | | 48 *4 | 121.8 | 52.2 | 240 | excellent |
| Example 10 | 6 | 12 *1 | | 144 *4 | 54.6 | 23.4 | 240 | excellent |
| Example 11 | 18 | 36 *1 | | 96 *4 | 63 | 27 | 240 | excellent |
| Example 12 | 18 | 36 *1 | | 144 *4 | 29.4 | 12.6 | 240 | good |
| Example 13 | 42 | 24 *1 | | 96 *4 | 12.6 | 5.4 | 240 | excellent |
| Example 14 | 18 | 36 *2 | | 144 *4 | 29.4 | 12.6 | 240 | good |
| Example 15 | 12 | | 24 *3 | 96 *4 | 75.6 | 32.4 | 240 | excellent |
| Example 16 | 18 | | 36 *3 | 96 *4 | 63 | 27 | 240 | excellent |
| Comp. Ex. 4 | 12 | 24 *1 | | 48 *5 | 109.2 | 46.8 | 240 | poor |
| Comp. Ex. 5 | 12 | 24 *1 | | 96 *5 | 75.6 | 32.4 | 240 | not flow |

*1 HPMCAS having 7.4 wt % hydroxypropoxyl groups, 23 wt % methoxyl groups, 9.3 wt % acetyl groups and 11.0 wt % succinyl groups was used.
*2 HPMCAS having 7.4 wt % hydroxypropoxyl groups, 23.5 wt % methoxyl groups, 7.3 wt % acetyl groups and 14.8 wt % succinyl groups was used.
*3 HPMCP having 6.1 wt % hydroxypropoxyl groups, 19.2 wt % methoxyl groups, and 33.2 wt % carboxybenzoyl groups was used.
*4 L-HPC of Sample 1 was used.
*5 L-HPC which was a same kind as one used in Comp. Ex. 2 was used.

TABLE 7-continued

| | dissoluton percentage (%)/ Japanese Pharmacopoeia 2nd fluid | | | | | | | JP 1st fluid |
|---|---|---|---|---|---|---|---|---|
| time (minutes) | 0 | 2 | 5 | 10 | 15 | 20 | 30 | 120 |
| Example 13 | 0 | 54.5 | 89.6 | 100 | 100 | 100 | 100 | 10% or less |
| Example 14 | 0 | 90.6 | 93.7 | 82.9 | 72.2 | 66 | | 61.4 10% or less |
| Example 15 | 0 | 74.5 | 74.5 | 74.5 | 69.9 | 68.4 | | 63.8 10% or less |
| Example 16 | 0 | 77.4 | 75.1 | 52.3 | 49.6 | 46.7 | | 46.7 10% or less |
| Comp. Ex. 4 | 0 | 60.5 | 57.1 | 46.6 | 45.8 | 44.5 | | 45.8 10% or less |
| Comp. Ex. 5 | not measurable because granulation was impossible | | | | | | | |
| nifedipine alone | 0 | 0.6 | 3.4 | 9.3 | 10 | 10.6 | 11.9 | |

Examples 17 to 25 and Comparative Example 6

Using the granulated products prepared in Examples 7 to 15 as powders for tableting, tablets were produced (Examples 17 to 25) as in Examples 4 to 6 in which 0.5% by weight of magnesium stearate was added as a lubricant and mixed with the powders for tableting. As a comparative example, using the granulated product prepared in Comparative Example 4 as a powder for tableting, a tablet was produced (Comparative Example 6) as in Examples 17 to 25. The obtained tablets were tested as in Examples 4 and 5, in terms of hardness, and disintegration in the 1st or 2nd fluid according to the Japanese Pharmacopoeia. Table 8 shows the results.

The tablets obtained in Examples 17 to 25 exhibited appropriate hardness and excellent disintegration (the 2nd fluid according to the Japanese Pharmacopoeia). On the other hand, in a case where the low-substituted hydroxypropylcellulose in Comparative Example 2 was added as the disintegrant (Comparative Example 6), good hardness and good disintegration (the 2nd fluid according to the Japanese Pharmacopoeia) were exhibited, but the tablet was disintegrated within 15 minutes in the 1st fluid according to the Japanese Pharmacopoeia.

<Drug Solubility of Examples 17 to 25 and Comparative Example 6>

Dissolution Test was performed as in Example 4, on 1890 mg of the tablets (containing 90 mg of nifedipine) obtained in Examples 17 to 25 and Comparative Example 6. Table 9 shows the results.

In the tablets obtained in Examples 17 to 25, the dissolution rate was by no means inferior to that from the granulated products. On the other hand, in the tablet obtained in Comparative Example 6, the solubility of the drug was not substantially improved.

In the tablets obtained in Examples 17 to 25, the rate of the drug dissolved after 120 minutes in the 1st fluid according to the Japanese Pharmacopoeia was 10% or less of the initial concentration of the drug administered. Furthermore, the dissolution rate within 10 minutes in the 2nd fluid according to the Japanese Pharmacopoeia was 70% or more. More specifically, the drug was dissolved in an excellent manner. Furthermore, in Dissolution Test using the 2nd fluid according to the Japanese Pharmacopoeia, the concentration and rate of the drug dissolved were significantly high compared with the solubility of the nifedipine bulk powder.

On the other hand, in a case where the low-substituted hydroxypropylcellulose of Comparative Example 2 was added as the disintegrant (Comparative Example 6), the rate of the drug dissolved after 120 minutes in the 1st fluid (artificial gastric juice) according to the Japanese Pharmacopoeia was 10% or less of the initial concentration of the drug administered, but the dissolution rate within 10 minutes in the 2nd fluid according to the Japanese Pharmacopoeia was less than 70%, that is, the solubility was not improved.

In the evaluation above, it has been confirmed that the tablets of the solid dispersions of the present invention have excellent disintegration, and allow the drug to be dissolved rapidly and at high rate.

TABLE 8

| | composition | | | | | | | | tablet | disintegration time | |
|---|---|---|---|---|---|---|---|---|---|---|---|
| | nifedipine (mg) | HPMCAS *1 (mg) | HPMCP (mg) | L-HPC (mg) | lactose (mg) | corn starch (mg) | St-Mg (mg) | total (mg) | hardness (kgf) | JP 2nd fluid (minutes) | JP 1st fluid (minutes) |
| Example 17 | 10 | 20 *1 | | 20 *4 | 105 | 45 | 1 | 201 | 7.3 | 6.2 | >30 |
| Example 18 | 10 | 20 *1 | | 80 *4 | 63 | 27 | 1 | 201 | 7.6 | 4.5 | >30 |
| Example 19 | 5 | 10 *1 | | 40 *4 | 101.5 | 43.5 | 1 | 201 | 6.2 | 3.4 | >30 |
| Example 20 | 5 | 10 *1 | | 120 *4 | 45.5 | 19.5 | 1 | 201 | 7.9 | 1.4 | >30 |
| Example 21 | 15 | 30 *1 | | 80 *4 | 52.5 | 22.5 | 1 | 201 | 7.3 | 4.5 | >30 |
| Example 22 | 15 | 30 *1 | | 120 *4 | 24.5 | 10.5 | 1 | 201 | 6.5 | 16.3 | >30 |
| Example 23 | 35 | 70 *1 | | 80 *4 | 10.5 | 4.5 | 1 | 201 | 9.8 | 4.2 | >30 |
| Example 24 | 15 | 30 *2 | | 120 *4 | 24.5 | 10.5 | 1 | 201 | 6.6 | 4.5 | >30 |
| Example 25 | 10 | | 20 *3 | 80 *4 | 63 | 27 | 1 | 201 | 5.8 | 4.1 | 28 |
| Comp. Ex. 6 | 10 | 20 *1 | | 40 *5 | 91 | 39 | 1 | 201 | 6 | 10.1 | 9.6 |

*1 HPMCAS having 7.4 wt % hydroxypropoxyl groups, 23 wt % methoxyl groups, 9.3 wt % acetyl groups, and 11.0 wt % succinyl groups was used.
*2 HPMCAS having 7.4 wt % hydroxypropoxyl groups, 23.5 wt % methoxyl groups, 7.3 wt % acetyl groups, and 14.8 wt % succinyl groups was used.
*3 HPMCP having 6.1 wt % hydroxypropoxyl groups, 19.2 wt % methoxyl groups, and 33.2 wt % carboxybenzoyl groups was used.
*4 L-HPC of Sample 2 was used.
*5 L-HPC which was a same kind as one used in Comp. Ex. 2 was used.

TABLE 9

| time (minutes) | dissolution percentage of drug (%)/ Japanese Parmacopoeia 2nd fluid | | | | | | | JP 1st fluid |
|---|---|---|---|---|---|---|---|---|
| | 0 | 2 | 5 | 10 | 15 | 20 | 30 | 120 |
| Example 17 | 0 | 56.2 | 68 | 72.5 | 68 | 63.6 | 54.7 | 10% or less |
| Example 18 | 0 | 84.1 | 95 | 87.2 | 76.3 | 68.5 | 59.2 | 10% or less |
| Example 19 | 0 | 52.2 | 78.3 | 67.6 | 56.8 | 52.2 | 44.5 | 10% or less |
| Example 20 | 0 | 86 | 82.9 | 64.5 | 55.3 | 50.7 | 44.5 | 10% or less |
| Example 21 | 0 | 37.1 | 65.9 | 74.2 | 78.3 | 78.3 | 75.6 | 10% or less |
| Example 22 | 0 | 44.5 | 50.7 | 74.1 | 74.1 | 61.8 | 58.8 | 10% or less |
| Example 23 | 0 | 34.9 | 61 | 75 | 90.7 | 100 | 100 | 10% or less |
| Example 24 | 0 | 33.3 | 59.2 | 70.4 | 70.4 | 67.9 | 43.2 | 10% or less |
| Example 25 | 0 | 77.4 | 45.1 | 32.4 | 29.6 | 26.7 | 25.4 | 10% or less |
| Comp. Ex. 6 | 0 | 44.6 | 53.1 | 60.2 | 45.2 | 44.2 | 47.7 | 10% or less |
| nifedipine alone | 0 | 0.6 | 3.4 | 9.3 | 10 | 10.6 | 11.9 | |

The invention claimed is:

1. A solid dosage form comprising an enteric solid dispersion,
   the dispersion comprising a poorly soluble drug, an enteric polymer and a disintegrant, wherein the disintegrant is compaction-ground low-substituted hydroxypropylcellulose having an average particle size of 10 to 100 μm and a specific surface area measured by BET method of at least 1.0 m$^2$/g, and wherein said disintegrant is compaction-ground low-substituted hydroxypropylcellulose having 5 to 16% by weight of hydroxypropyl groups.

2. The solid dosage form comprising the enteric solid dispersion according to claim 1, further comprising an excipient.

3. The solid dosage form comprising the enteric solid dispersion according to claim 1, wherein said disintegrant is compaction-ground low-substituted hydroxypropylcellulose having a bulk density of at least 0.30 g/ml.

4. The solid dosage form comprising the enteric solid dispersion according to claim 1, wherein said disintegrant is compaction-ground low-substituted hydroxypropylcellulose having an elastic recovery ratio of not greater than 7% when compressed at a compression force of 50 MPa.

5. The solid dosage form comprising the enteric solid dispersion according to claim 1, wherein said disintegrant is compaction-ground low-substituted hydroxypropylcellulose having a swollen volume increase ratio of at least 300% and a swollen volume increase rate of at least 100%/min when absorbing water.

6. The solid dosage form comprising the enteric solid dispersion according to claim 1, wherein said disintegrant is compaction-ground low-substituted hydroxypropylcellulose having a repose angle of not greater than 42°.

7. The solid dosage form comprising the enteric solid dispersion according to claim 1, wherein said enteric polymer is one selected from the group consisting of cellulose acetate phthalate, cellulose acetate trimellitate, cellulose acetate succinate, methylcellulose phthalate, hydroxymethylcellulose ethyl phthalate, hydroxypropylmethylcellulose phthalate, hydroxypropylmethylcellulose acetate succinate, hydroxypropylmethylcellulose acetate maleate, hydroxypropylmethylcellulose trimellitate, carboxymethylethylcellulose, polyvinyl butyrate phthalate, polyvinyl alcohol acetate phthalate, methacrylic acid/ethyl acrylate copolymer, methacrylic acid/methyl methacrylate copolymer, and methacrylic acid copolymer.

8. The solid dosage form comprising the enteric solid dispersion according to claim 2, wherein said disintegrant is compaction-ground low-substituted hydroxypropylcellulose having a bulk density of at least 0.30 g/ml.

9. The solid dosage form comprising the enteric solid dispersion according to claim 2, wherein said disintegrant is compaction-ground low-substituted hydroxypropylcellulose having an elastic recovery ratio of not greater than 7% when compressed at a compression force of 50 MPa.

10. The solid dosage form comprising the enteric solid dispersion according to claim 2, wherein said disintegrant is compaction-ground low-substituted hydroxypropylcellulose having a swollen volume increase ratio of at least 300% and a swollen volume increase rate of at least 100%/min when absorbing water.

11. The solid dosage form comprising the enteric solid dispersion according to claim 2, wherein said disintegrant is compaction-ground low-substituted hydroxypropylcellulose having a repose angle of not greater than 42°.

12. The solid dosage form comprising the enteric solid dispersion according to claim 2, wherein said enteric polymer is one selected from the group consisting of cellulose acetate phthalate, cellulose acetate trimellitate, cellulose acetate succinate, methylcellulose phthalate, hydroxymethylcellulose ethyl phthalate, hydroxypropylmethylcellulose phthalate, hydroxypropylmethylcellulose acetate succinate, hydroxypropylmethylcellulose acetate maleate, hydroxypropylmethylcellulose trimellitate, carboxymethylethylcellulose, polyvinyl butyrate phthalate, polyvinyl alcohol acetate phthalate, methacrylic acid/ethyl acrylate copolymer, methacrylic acid/methyl methacrylate copolymer, and methacrylic acid copolymer.

* * * * *